United States Patent [19]

Senia et al.

[11] Patent Number: 4,850,867

[45] Date of Patent: Jul. 25, 1989

[54] ENDODONTIC INSTRUMENT

[75] Inventors: E. Steve Senia; William L. Wildey, both of San Antonio, Tex.

[73] Assignee: Board of Regents, The University of Texas System, Austin, Tex.

[21] Appl. No.: 152,464

[22] Filed: Feb. 5, 1988

[51] Int. Cl.[4] .............................................. A61C 5/02
[52] U.S. Cl. .................................................... 433/102
[58] Field of Search ........................................ 433/102

[56] References Cited

U.S. PATENT DOCUMENTS

| D. 283,840 | 5/1986 | Matsutani . | |
| 636,359 | 11/1899 | Schultz | 433/102 |
| 4,299,571 | 11/1981 | McSpadden | 433/102 |
| 4,443,193 | 4/1984 | Roane | 433/102 |
| 4,536,159 | 8/1985 | Roane | 433/224 |

FOREIGN PATENT DOCUMENTS

| 631469 | 5/1936 | Fed. Rep. of Germany | 433/102 |
| 2524105 | 4/1976 | Fed. Rep. of Germany | 433/102 |

OTHER PUBLICATIONS

ISO Standard 3630/2, First edition-1986-05-01.
ANSI/ADA Specification No. 28-1981, approved Oct. 9, 1981.
Mani Apical Reamer.
Caulk Gates-Glidden drills.
Caulk Dynatrak.
Hygenic Endodontic Cutting Instruments.
flex-R.
Photograph of unknown endodontic instrument.
Brochure for the Mani Apical Reamer.
Pathways of the Pulp, pp. 340-242 (1980).
The American Textbook of Operative Dentistry, pp. 452-463 (1900).
Journal of Endodontics 12:293-300 (1986), Powell et al.
Journal of the American Dental Association 113:(596-597) 1986, Roane et al.
The Dentists Desk Reference, pp. 248-262 (1981).
Journal of the American Dental Association 58:85-92 (1959), Luks.
Clinical Endodontics, pp. 301-318 (1956).
The Dental Cosmos 54:56 (1912).
The Dental Cosmos 64:113-1148 (1922).
Oral Surgery 14:83-91 (1961), Ingle.
Journal of Endodontics 11:435-441 (1985), Miserendino et al.
Journal of Endodontics 11:212-217 (1985), Anderson et al.
Journal of Endodontics 11:110-116 (1985), Boger et al.
Journal of Endodontics 8:253-259 (1982), Felt et al.
Journal of Endodontics 8:260-264 (1982), Dolan et al.
Oral Surgery 50:566-568 (1980), Martin et al.
Oral Surgery 8:1211-1213 (1955), Ingle.
British Dental Journal 137:239-244 (1974), Harty et al.
The Dental Cosmos 65:1072-1091 (1923), Kells.
ISO Standard 3630, First edition-1984-02-15.
Jun. 1988, Dental Products Report.
Johnson paper, p. 185.

Primary Examiner—Robert Peshock
Attorney, Agent, or Firm—Arnold, White & Durkee

[57] ABSTRACT

An endodontic instrument in accordance with the present invention includes a substantially non-cutting pilot segment, a relatively short cutting segment, and a flexible shaft segment, which can have a handle at its distal end for manual manipulation, or an adapter for attachment to a mechanical handpiece. The non-cutting pilot, the short length of the cutting segment, and the flexibility of the shaft combine to allow the instrument to be used in curved root canals without causing undue change in the natural root canal contours.

13 Claims, 3 Drawing Sheets

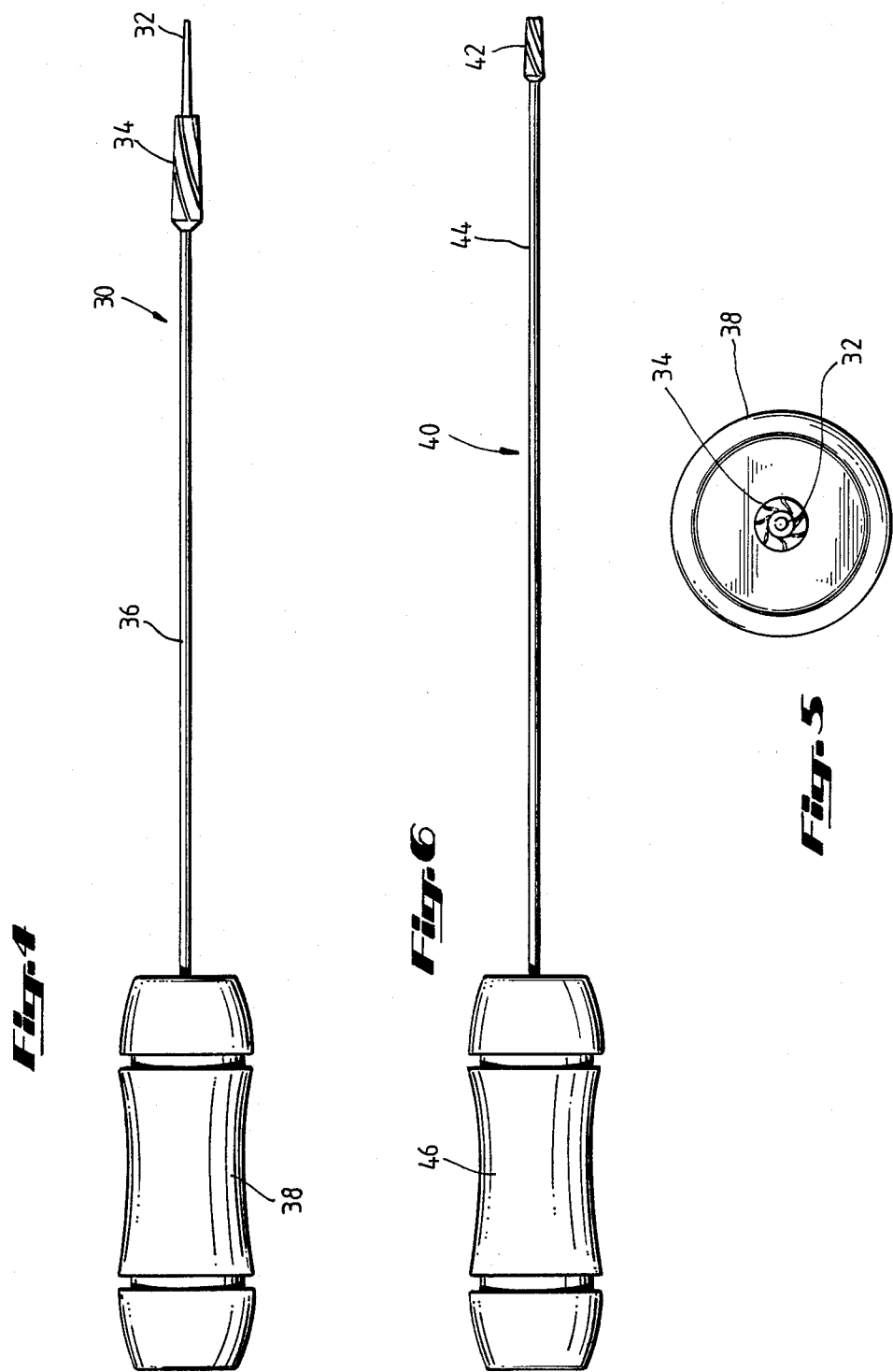

ENDODONTIC INSTRUMENT

FIELD OF THE INVENTION

The present invention relates to instruments which can be used in endodontic (root canal) therapy. More specifically, the present invention concerns an endodontic instrument which can clean and shape both straight and curved canals.

BACKGROUND OF THE INVENTION

Endodontic therapy is performed to save a tooth when the pulp, the soft tissue in the center of the tooth, becomes infected or damaged. The therapy includes opening the tooth, removing the pulp, cleaning, shaping, and smoothing the dentinal walls, and then filling the tooth. It is important, and in fact necessary, that the pulp be removed not only from the pulp chamber in the crown of the tooth but also from the root canals which extend to the apices (at the root end) of the tooth. Failure to completely remove the pulp can render the entire procedure ineffective, leading to loss of the tooth.

A wide variety of instruments, such as files, reamers, rasps, broaches, and probes, have been developed over the years for use in removing the pulp and cleaning, shaping, and smoothing the walls of the root canal. One example is the K-type file, which is formed from a blank which usually has a square cross section. By tightly twisting the blank, a file having continuous spiral cutting edges is formed. A K-type reamer is formed in much the same fashion, although usually with a looser twist, and usually from a blank with a triangular cross section. A K-flex file is similar to the standard K-type file, except it is formed by twisting a blank with a rhomboid cross section. Another example is the H-type (Hedstrom) file, which is made by machining a cylindrical blank to form a helical cutting edge. All of the instruments described above become successively larger from the top toward the handle, usually for a length of 16 mm.

Many of these instruments are designed to be manipulated by hand, typically having a handle at their distal end. Others are adapted to be held in a mechanical hand piece. Hand manipulated root canal instruments achieve their cutting and cleaning objectives by being rotated, or by being moved in and out of the root canal along the instrument's longitudinal axis. Mechanically manipulated instruments achieve their cutting and cleaning objectives by being vibrated from side to side, rotated, moved in and out longitudinally, or by a combination of longitudinal and rotational movement.

When cleaning and shaping a root canal, the desired goal is to produce a funnel-shaped canal, with the smaller end at the apical foramin (hole). This funnel shape makes it easier to fill the root canal. At the same time, great efforts are made not to remove too much dentin, because that can weaken the structural integrity of the tooth.

Even with the wide diversity of available instruments, there are some common problems in endodontic therapy for which no existing instrument provides a very satisfactory solution. For example, the multiple root canals in molars are usually curved, in addition to having an extremely small canal diameter which becomes even smaller at their apices. The curvature is three dimensional, and frequently is irregular from point to point in a given root canal. This combination of curvature and small diameter makes it extremely difficult to ensure complete pulp removal and satisfactory cleaning, shaping, and smoothing of the dentinal walls without removing excessive dentin and thus changing the curvature of the canal and weakening the root structure. Various embodiments of this undesired result are referred to as transportation, ledging, and zipping. Conservative therapy using instruments which have smaller diameters can help avoid ledging, transportation, and zipping, but tends to leave too much pulp in the root canal, which is very undesirable.

This difficulty is compounded by the length of the cutting surface on most endodontic instruments. Most such instruments are designed to cut along most of their length, and this makes the undesired results listed above even harder to avoid.

There is a long-standing need for an instrument which can clean and shape curved root canals while maintaining as much as possible the original configuration of the canal.

SUMMARY OF THE INVENTION

An endodontic instrument in accordance with the present invention can be used in a human tooth which has at least one root canal. It includes (a) a substantially non-cutting pilot segment which has a diameter small enough to allow it to enter the apical area of the root canal of a human tooth and which acts as a guide to follow the canal to the apex;

(b) a flexible shaft segment; and (c) a cutting segment which is located between the pilot segment and the shaft, the cutting segment having a length no greater than about 14 mm.

In one specific embodiment of the present invention, the instrument includes (a) a substantially non-cutting pilot segment which has a proximal and distal end, and which has a diameter between about 0.009 and 1.0 mm, and which is between about 0.01 and 14 mm long;

(b) a cutting segment which has a proximal and distal end, the proximal end being attached to the distal end of the pilot segment, and which has a diameter between about 0.01 and 2.0 mm, and which is between about 0.5 and 14 mm long; and (c) a flexible shaft segment which has a proximal and distal end, the proximal end being attached to the distal end of the cutting segment, and which has a diameter no greater than the largest diameter of the cutting segment, and which is between about 10 and 28 mm long.

There are several important distinctions between the present invention and previous endodontic instruments. The tip of an instrument in accordance with the present invention is a substantially noncutting pilot, while most standard instruments have a cutting tip. This pilot acts as a guide which follows the root canal. Also, the cutting segment of instruments in accordance with the present invention is quite short compared to standard instruments, the latter usually having cutting surfaces 16 mm long. This shorter cutting length provides the dentist with substantially improved control over where cutting of dentin occurs. Further, the shaft used in the present invention is more flexible than shafts in comparable standard instruments.

These and other distinctions combine to make the present invention extremely advantageous for effectively performing endodontic therapy. Instruments in accordance with the present invention can more easily follow the natural curvature of the entire root canal, and therefore cause much less unintended cutting of dentin and change of the natural curvature.

A variation of the present invention comprises a cutting segment whose length is no greater than about 14 mm; and a shaft whose proximal end is attached to the distal end of the cutting segment. This particular variation is suited for cleaning the apical 0.75 mm of the root canal of a human tooth, i.e., the most apical part of the root canal not cleaned by the non-cutting pilot of the previous embodiments.

BRIEF DESCRIPTION OF THE DRAWINGS

FIG. 4 shows an endodontic instrument in accordance with the present invention with a handle mounted on its distal end.

FIG. 5 shows an end view of an instrument such as that shown in FIG. 4, with the instrument's proximal end being frontmost.

FIG. 6 shows an endodontic instrument in accordance with the present invention which does not have at its proximal end a non-cutting pilot segment.

DETAILED DESCRIPTION OF A SPECIFIC EMBODIMENT

Figure 1A:
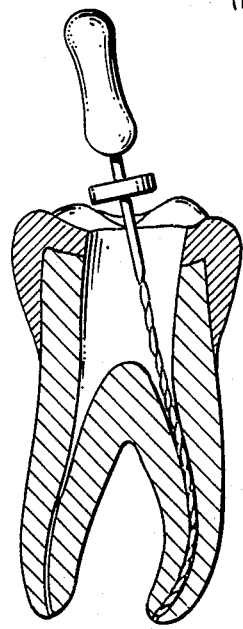
FIG. 1 shows the use of a prior art endodontic instrument and an inherent problem in its use.
Figure 1B:
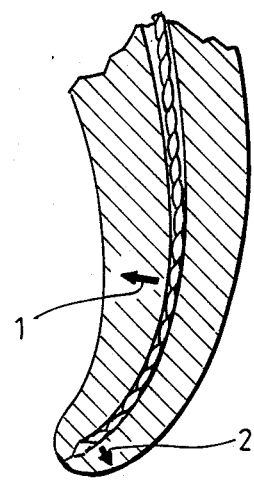
Figure 1C:
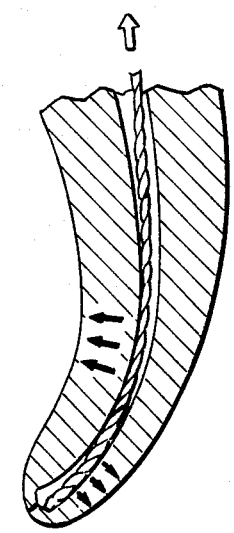
Figure 2A:
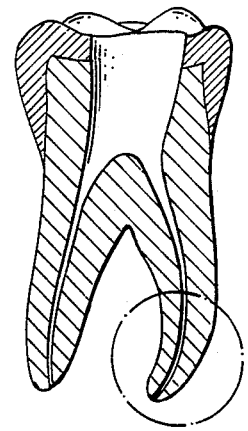
FIG. 2 shows four different problems caused by prior art instruments.
Figure 2B:
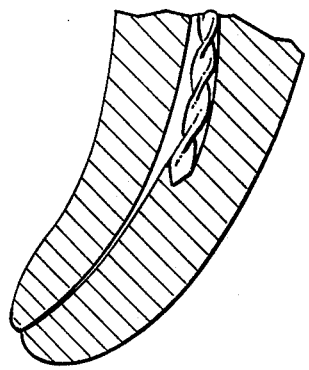
Figure 2C:
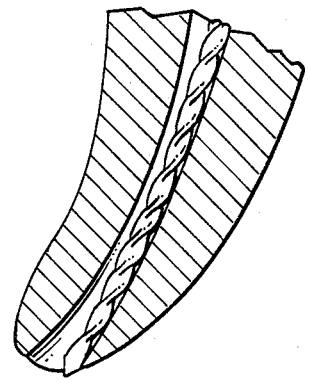
Figure 2D:
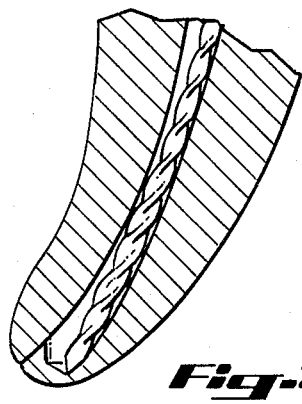
Figure 2E:
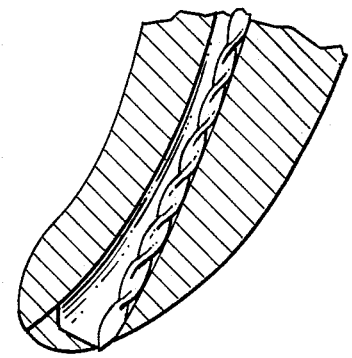

FIG. 1 shows how a prior art endodontic instrument is inserted into the root canal of a tooth. In FIG. 1A, the instrument has a small enough diameter so that it is sufficiently flexible to bend around the curvature of the root canal. FIG. 1B illustrates the forces at work when the instrument is at rest in a curved root canal. Under basic lever and fulcrum principles, the inherent rigidity of the instrument causes a force 1 to be exerted on the root canal wall in its middle. A corresponding forcre 2 is exerted on the opposite root canal wall near the apex of the canal. When the instrument is withdrawn, as shown in FIG. 1C, these forces are effectively increased and applied in a way that causes undesired cutting of the root canal walls. The force 3 acting near the middle of the root canal causes greatly enhanced cutting at that point during withdrawal. Even worse, the lever arm length below this fulcrum point is being decreased as the instrument is withdrawn, thereby increasing the force acting at the lower end. This increased force 4 digs away dentin at the apical end of the root canal, as can be seen in FIG. 1C.

FIG. 2 shows several problems that result from prior art instruments. FIG. 2A shows a typical curved root canal. FIG. 2B shows that instruments which have insufficient flexibility in relation to the diameter of their cutting segment, as mahy prior art instruments do, tend to form a ledge. Once such a ledge is formed, it is very difficult to advance an instrument beyond it. In FIG. 2C, the phenomenon shown in FIG. 1 has caused transportation of the apical foramen. This tends to make the filling that will be inserted into the tooth spill out into the surrounding tissue, which is very undesirable. In FIG. 4D, a similar effect known as zipping has occurred. In FIG. 4E the zipping is so pronounced that the side of the root has actually been perforated, which again will cause filling to spill out into the surrounding tissue.

An endodontic instrument in accordance with the present invention can include three principle parts: a substantially non-cutting pilot tip segment, a cutting segment, and a flexible shaft segment. The pilot segment can be either totally non-cutting, with a smooth surface, or it can have some minimal cutting or abrasive surface to give it a very minor cutting effect. The term "substantially non-cutting" is intended to cover both of these possibilities.

Figure 3:
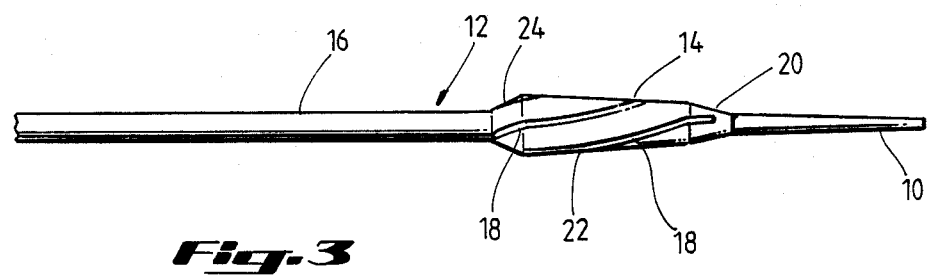
FIG. 3 shows an endodontic instrument in accordance with the present invention.

In FIG. 3, the non-cutting pilot segment 10 is a smooth tapered cylinder located at the proximal end of the instrument 12. The distal end of the pilot segment 10 is attached to the proximal end of the cutting segment 14. The distal end of the cutting segment 14 is attached to the shaft segment 16. The shaft segment 16 will normally have a circular cross section.

The substantially non-cutting pilot segment 10 is preferably a smooth tapered cylinder with a blunt or rounded (bullet shaped) proximal end. However, it would also be possible to use a pilot segment which has some raised edges or other projections on its surface, as long as they do not cause the pilot segment to have a substantial cutting effect. A goal of the pilot segment 10 is to serve as a guide for the cutting segment 14, not to perform a significant amount of cutting itself.

The cutting segment 14 depicted in FIG. 3 includes a plurality of spiral cutting edges 18, similar to the cutting portion of a K-type file. This embodiment of the cutting segment can have any number of configuration of cutting edges, preferably from 1–12 such edges. The cutting segment 14 could also be flattened, rather than cylindrical. In a flattened cutting segment, the two outer edges and the front edges would normally do the cutting. The cross section of such a cutting segment would be a relatively thin rectangle. The tightness of the spiral can also be increased, or decreased, even to the point of having no spiral. The cutting segment 14 could also be flattened, rather than cylindrical. In a flattened cutting segment, the two outer edges and the front edges would normally do the cutting. The cross section of such a flattened cutting segment would be a relatively thin rectangle. The cutting segment 14 could alternatively employ any cutting apparatus known to those skilled in this field, such as a K-flex cutting configuration, an H-type cutting configuration, a diamond cutting surface, or other cutting or abrasive materials.

The dimensions of the instrument are very important in achieving the desired results. The diameter of the pilot segment at its widest point is preferably about 0.17 mm but can range between about 0.009 and 1.0 mm. The diameter of the cutting segment at its widest point is preferably between about 0.01 and 2.0 mm, most preferably between about 0.20 and 1.4 mm. The diameter of the shaft segment should preferably be less than the diameter of the cutting segment at the latter's widest point, in order to increase flexibility and provide space for pulp and dentin debris to be removed from the canal. However, the diameter of the shaft segment could be equal to or greater than the diameter of the cutting segment. The shaft diameter will usually be between about 0.2 and 0.8 mm.

The pilot segment is preferably between about 0.01 and 14 mm long, most preferably between about 0.75 and 3 mm. The cutting segment is preferably between about 0.5 and 14 mm long, most preferably between about 0.5 and 4.0 mm long. The shaft is preferably between about 10 and 28 mm long.

The shaft segment will usually be solid, but could optionally be in the form of a helically wound spring coil, or a flat metal strip wrapped in a helical fashion to form an elongated cylindrical enclosure.

The pilot segment 10 and cutting segment 14 can be tapered or nontapered. The shaft 16 will usually have a constant diameter, but could also be tapered. If tapering is used in the pilot segment 10, it will usually increase in diameter from its proximal end to its distal end. The cutting segment 14 can suitable be tapered in three portions. A first transition portion 20 increases in diameter from the distal end of the pilot segment 10 until it meets a body portion 22. The body portion 22 also increases in diameter towards its distal end, but at a lesser angle than the first transition portion 20. The body portion 22 connects at its distal end to a second transition portion 24 which decreases in diameter from its proximal end to its distal end, where the second transition portion 24 connects to the shaft 16. This is only one possible configuration of the cutting segment 14. Others could be used also, including a reverse taper whereby the proximal end diameter of the cutting segment is greater than the distal end diameter, or any other combination.

The cutting segment 14 as shown in FIG. 1 will typically have cutting edges 18 or other abrasive means extending the entire length of one, two, or all three portions 20, 22, and 24.

Four examples are given below of specific dimensions for instruments as shown in FIG. 3. Example 1C is of an instrument whose cutting segment 14 does not have a first transition portion 20; i.e., the distal end of the pilot segment 10 is connected directly to the body portion 22.

TABLE 1

Length (mm) OF PILOT AND CUTTING SEGMENTS OF PILOT AND CUTTING SEGMENTS

| | PILOT SEGMENT | CUTTING SEGMENTS | | |
|---|---|---|---|---|
| | | 1ST TRANS. PORTION | BODY PORTION | TRANS. PORTION |
| Example 1A | 3.75 | 0.25 | 3.0 | 0.25 |
| Example 1B | 2.25 | 0.25 | 1.5 | 0.25 |
| Example 1C | 1.0 | 0 | 1.5 | 0.25 |
| Example 1D | 0.75 | 0.25 | 1.0 | 0.25 | a portion if they were extended to the point where they would converge.)

FIG. 4 shows an instrument 30 in accordance with the present invention which has a pilot segment 32, a cutting segment 34, a shaft segment 36, and a handle 38. The handle 38 is adapted to be grasped by a dentist's hand, allowing him to manipulate the instrument and direct its proximal end in a patient's root canal.

FIG. 5 shows an end view of the instrument of FIG. 4. The pilot segment 32 has a smaller diameter than the cutting segment 34. The shaft segment 36 is not visible in FIG. 5 because in this particular embodiment it has a smaller diameter than the cutting segment 34. The handle 38 is at the distal end of the instrument.

Alternatively, the handle 38 could be replaced by an adapter for use with a mechanical handpiece for vibrating or rotating the instrument 30. "Mechanical handpiece" is used in this patent application to included handpieces which are driven by electronic motors or pneumatic means, such as sonic, ultrasonic, or conventional handpieces. Commercially available mechanical handpieces include the Giromatic, Endolift, and Endosonic devices. The working motion of an instrument in accordance with the present invention can be rotational (either clockwise or counterclockwise, from 0° to 360° or greater), in and out along the longitudinal axis of the instrument, from side to side, or any combination of these.

The pilot segment, cutting segment, and shaft segment can be made from a variety of materials known to those skilled in the art, such as stainless steel. They are preferably ground from a single blank. The cutting segment can be formed by, for example, grinding the cutting edges in their desired final configuration. It can also be formed by grinding this segment to have a polygonal cross-section (e.g., triangular, square, or rhomboid) and then twisting it to form a plurality of spiral cutting edges.

Because of the relatively small diameter of the instrument, especially in its shaft segment, the instrument will have a significant degree of flexibility. This is very important in allowiang the instrument to follow a curved root canal.

Instruments in accordance with the present invention will preferably have a bending moment, when measured in accordance with ISO standard 3630-1984(e), section 7.3, of no greater than about 120 g-cm. The bending moment is most preferably no greater than about 80 g-cm.

TABLE 2

DIAMETER (mm) OF SEGMENTS OF ENDODONTIC INSTRUMENTS

| | PILOT SEGMENT | CUTTING SEGMENT | | | SHAFT SEGMENT |
|---|---|---|---|---|---|
| | | 1ST TRANS. PORTION (DISTAL END) | BODY PORTION (DISTAL END) | 2ND TRANS. PORTION (DISTAL END) | |
| Ex. 1A | 0.15 | 0.5 | 0.6 | 0.4 | 0.4 |
| Ex. 1B | 0.15 | 0.35 | 0.5 | 0.3 | 0.3 |
| Ex. 1C | 0.15 | none | 0.35 | 0.2 | 0.2 |
| Ex. 1D | 0.15 | 0.30 | 0.32 | 0.35 | 0.30 |

The angle of taper on the first transition portion 20 of the cutting segment can be anywhere between about 0° and 180°, but is preferably about 75°. Angles even greater than 180° could be used, but would not normally be desirable. (All angles in this patent are stated according to the ISO standard, meaning that the number given is the included angle between the two opposite sides of The ISO standard referred to in the preceding paragraph, which is incorporated in this patent by reference, basically involves removing the handle from an instrument and then placing the instrument (minus the handle) into test apparatus which will deflect the instrument to a 45° angle. One tip of the instrument is placed into the jaws of a chuck to a depth of about 3 mm, the chuck is tightened, a catch pin contacts the opposite end of the instrument, and torque measuring equipment is put in place. When 45° deflection has been achieved, the device will stop and a reading can be taken.

FIG. 6 shows an alternate instrument 40 in accordance with the present invention, which includes a cutting segment 42, a shaft segment 44 and a handle 46, but no pilot segment. The dimensions of the cutting segment and shaft segment are preferably the same as those listed above for the embodiment of FIG. 1, except that the cutting segment in a preferred embodiment can be as short as about 0.1 mm. This alternative embodiment can be used advantageously to clean the apical 0.75 mm of a root canal.

The preceding description is intended to illustrate specific embodiments of the present invention, but not to describe every possible embodiment of the invention. Those skilled in this field will recognize that modifications could be made which would remain within the scope of this invention.

We claim:

1. An endodontic instrument for use in a human tooth which has at least one root canal, including:
   a substantially non-cutting pilot segment which has a proximal and distal end, which has a diameter between about 0.009 and 1.0 mm, and which is between about 0.01 and 14 mm long, the pilot segment acting as a guide to follow the canal to the apex;
   a cutting segment which has a proximal and distal end, the proximal end being attached to the distal end of the pilot segment, and which has a diameter between about 0.01 and 2.0 mm, and which is between about 0.5 and 14 mm long; and
   a shaft which has a proximal and distal end, the proximal end being attached to the distal end of the cutting segment, and which is between about 10 and 28 mm long; and
   whereby the bending moment of the instrument as measured in accordance with ISO standard 3630-1984(E), section 7.3, is no greater than about 120 g-cm.

2. The instrument of claim 1, further including a handle mounted on the distal end of the shaft.

3. The instrument of claim 1, further including an adapter located at the distal end of the shaft segment which can be held and powered by a mechanical handpiece.

4. The instrument of claim 1, where the cutting segment is between about 0.5 and 4.0 mm long.

5. An endodontic instrument for use in a human tooth which has at least one root canal, including:
   a substantially non-cutting pilot segment which has a proximal and distal end, which has a diameter between about 0.009 and 1.0 mm, and which is between about 0.75 and 3.0 mm long, the pilot segment acting as a guide to follow the canal to the apex;
   a cutting segment which has a proximal and distal end, the proximal end being attached to the distal end of the pilot segment, and which has a diameter between about 0.2 and 1.4 mm, and which is between about 0.5 and 4.0 mm long;
   a shaft segment which has a proximal and distal end, the proximal end being attached to the distal end of the cutting segment, and which is between about 10 and 28 mm long; and
   whereby the bending moment of the instrument as measured in accordance with ISO standard 3630-1984(E), section 7.3, is no greater than about 120 g-cm.

6. The instrument of claim 5, where the shaft segment's diameter is no greater than the diameter of the cutting segment at the cutting segment's largest point.

7. An endodontic instrument for use in a human tooth, the tooth having at least one root canal, including:
   a cutting segment which has a proximal and distal end and whose length is no greater than about 14 mm;
   a shaft segment which has a proximal and distal end and whose proximal end is attached to the distal end of the cutting segment; and
   whereby the bending moment of the instrument as measured in accordance with ISO standard 3630-1984(E), section 7.3, is no greater than about 120 g-cm.

8. The instrument of claim 7, further including a handle mounted on the distal end of the shaft segment.

9. The instrument of claim 7, further including an adapter located at the distal end of the shaft segment which can be held and powered by a mechanical handpiece.

10. The instrument of claim 7, where the diameter of the cutting segment is between about 0.01 and 2.0 mm.

11. The instrument of claim 10, where the diameter of the cutting segment at its largest point is between about 0.20 and 1.4 mm, and the diameter of the shaft is between about 0.2 and 0.8 mm.

12. The instrument of claim 7, where the length of the cutting segment is between about 0.1 and 14 mm, and the length of the shaft segment is between about 10 and 28 mm.

13. The instrument of claim 12, where the length of the cutting segment is between about 0.1 and 4.0 mm.

* * * * *